United States Patent [19]

Curran

[11] 3,991,060
[45] Nov. 9, 1976

[54] 5,6,7,8 TETRAHYDROQUINOLINE DERIVATIVES

[75] Inventor: Adrian Charles Ward Curran, Gosforth, England

[73] Assignee: John Wyeth & Brother Limited, Maidenhead, England

[22] Filed: Apr. 15, 1975

[21] Appl. No.: 568,359

[30] Foreign Application Priority Data

Apr. 19, 1974 United Kingdom............... 17222/74

[52] U.S. Cl........................... 260/287 T; 260/283 S; 260/283 CN; 260/294.9; 260/295 F; 260/289 K; 260/289 R; 260/586 R; 260/294.8 C
[51] Int. Cl.²............... C07D 215/20; C07D 215/48
[58] Field of Search............. 260/287 T, 283 CN, 260/283 S, 294.8 C, 295 F, 294.9

[56] References Cited
UNITED STATES PATENTS

| | | | |
|---|---|---|---|
| 3,632,590 | 1/1972 | Leroi............................... | 260/287 L |
| 3,692,790 | 9/1972 | Archer............................ | 260/287 F |
| 3,726,878 | 4/1973 | Kanai et al...................... | 260/283 S |
| 3,751,418 | 8/1973 | Weyer............................. | 260/287 F |
| 3,813,398 | 5/1974 | Aumuller........................ | 260/287 F |

*Primary Examiner*—Nicholas S. Rizzo
*Assistant Examiner*—David E. Wheeler

[57] ABSTRACT

The invention provides a compound of formula I

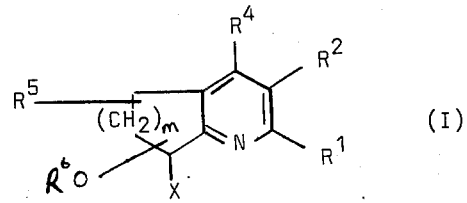

or an acid addition salt thereof, wherein $R^1$, $R^2$ and $R^4$ are the same or different and represent hydrogen, or a lower alkyl radical, $R^5$ represents hydrogen or single or multiple substitution by lower alkyl radicals, X is cyano, $CONHR^3$, $CSNHR^3$ or $CO_2R^3$ wherein $R^3$ is hydrogen or a lower alkyl radical, m is 1, 2 or 3 and $R^6$ is hydrogen, a lower alkyl radical or a lower alkanoyl radical or an alkali-metal salt of a compound in which X is $CO_2H$.

Compounds of formula I wherein X is CN or $CSNHR^3$ and $R^6$ is lower alkyl are anti-ulcer agents. The other compounds of formula I are intermediates.

9 Claims, No Drawings

5,6,7,8 TETRAHYDROQUINOLINE DERIVATIVES

The invention relates to novel pyridine derivatives and to process for preparing them.

The invention provides a compound of formula I

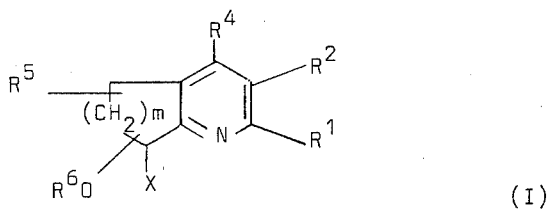

(I)

or an acid addition salt thereof, wherein $R^1$, $R^2$ and $R^4$ are the same or different and represent hydrogen, or a lower alkyl radical, $R^5$ represents hydrogen or single or multiple substitution by lower alkyl radicals, X is cyano, $CONHR^3$, $CSNHR^3$ or $CO_2R^3$ wherein $R^3$ is hydrogen or a lower alkyl radical, $m$ is 1, 2 or 3 and $R^6$ is hydrogen, a lower alkyl radical or a lower alkanoyl radical, or an alkali-metal salt of a compound in which X is $CO_2H$.

$R^5$ or $OR^6$ may be in the same position as X or on the same carbon atom as each other (excluding that carrying X).

When any of $R^1$, $R^2$, $R^3$, $R^4$ or $R^5$ is a lower alkyl radical it may be a straight or branched chain, having from 1 to 6 carbon atoms, e.g. methyl, ethyl, $n$-, and iso-propyl and $n$-, $s$- and $t$-butyl, $R^5$ may be a gem-dimethyl group and when a single radical may be on the same carbon atom as the group X if $OR^6$ is on a different carbon atom. The term alkyl radical is also intended to embrace cyclic alkyl radicals e.g. cyclobutyl, cyclopentyl and cyclohexyl. $R^6$ may be any of the lower alkyl radicals mentioned above, preferably methyl.

Particularly preferred compounds are those in which one of $R^1$, $R^2$ and $R^4$ is methyl and the others are hydrogen. Preferably $R^2$ is methyl and $R^1$ and $R^4$ are hydrogen. Also preferred are compounds wherein $m$ is 2. Compounds wherein $R^3$ is selected from hydrogen and methyl are also preferred.

Thus the present invention provides, in one preferred aspect, compounds of formula II

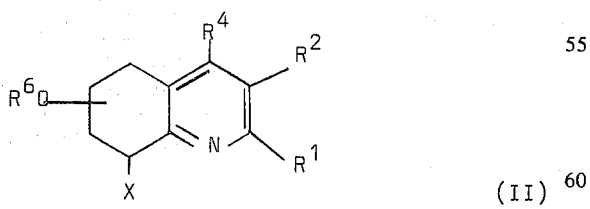

(II)

and acid addition salts thereof, wherein $R^1$, $R^2$ and $R^4$ are selected from hydrogen and methyl and X is CN, $CONHR^3$, $CSNHR^3$ or $CO_2R^3$, $R^3$ and $R^6$ being as defined in connection with formula I, and metal e.g. alkali metal salts of those compounds wherein X is $CO_2H$. In formula II, it is preferred that X is $CSNH_2$, or $CSNHCH_3$ and only one of $R^1$, $R^2$ and $R^4$ is methyl.

The compounds of formula I can form acid addition salts with inorganic acids e.g. hydrochloric, hydrobromic, sulphuric or nitric acids, or organic acids e.g. citric, fumaric, maleic or tartaric acids. These acid addition salts are included in the invention.

In the compounds of formula I the carbon atom to which X is attached is asymmetric. Consequently the compounds can exist in optically active $d$ and $l$ forms. These optically active forms and the racemates are included in the invention. The optically active forms may be separated by standard techniques either by formation of an acid salt with an optically active acid or by use of an optically active base with a compound in which X is COOH and subsequent conversion of the separated isomers to the desired compound.

Compounds of formula I, wherein X is CN or $CSNHR^3$, and $R^6$ is lower alkyl are anti-ulcer agents which display activity either in the anti-ulcer test method of Brodie and Hanson, J. Applied Physiology 15, 291, 1960 or the anti-secretory test of H. Shay, D. Sun and H. Greenstein, Gastroenterology 1954, 26, 906–13.

Compounds of formula I in which X is CN are also intermediates for the thioamides of formula I in which X is $CSNHR^3$. Compounds of formula I wherein X is $CONHR^3$ and $CO_2R^3$ are intermediates for preparation of compounds of formula I wherein X is $CSNHR^3$. Compounds of formula I wherein $R^6$ is hydrogen or lower alkanoyl are intermediates for the corresponding compounds where $R^6$ is lower alkyl.

The compounds of formula I may be prepared by various methods all of which are included in the invention.

A general method of preparing the compounds of formula I comprises treating a corresponding compound in which X is hydrogen to introduce the desired group X, e.g. by known methods. One group of starting materials for compounds of formula I are compounds of formula III

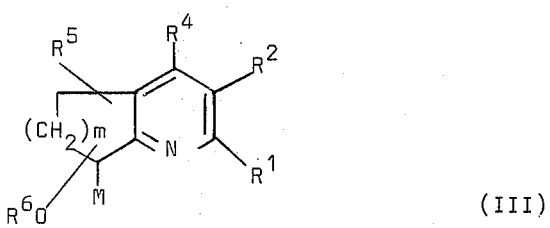

(III)

wherein $R^1$, $R^2$, $R^3$, $R^4$, $R^5$, $R^6$ and $m$ are as defined in connection with formula I and M is sodium, potassium, lithium or MgHal where Hal is chlorine, bromine or iodine.

Compounds of formula III wherein M is sodium, potassium or lithium may be prepared by reacting a compound of formula I wherein X is hydrogen with a metal alkyl $MR^7$ where $R^7$ is alkyl, aryl or aralkyl. The alkyl, aryl or aralkyl radical $R^7$ may have any of the values discussed above for the similar radicals $R^1$ and $R^2$. $R^7$ is preferably n-butyl or phenyl. Preferred compounds $MR^7$ are n-butyl lithium and phenyl lithium. It may be necessary to conduct this reaction at low temperature e.g. $-60°$ C to $-10°$ C such as $-40°$ C to $-20°$ C.

Compounds of formula III wherein M is MgHal may be prepared by testing a compound of formula I wherein X is hydrogen, with an alkyl magnesium halide, $R^8MgHal$ wherein $R^8$ is an alkyl group, preferably a lower alkyl group and Hal is chlorine, bromine or iodine. $R^8$ may be a straight or branched chain alkyl group, the iso-propyl group being preferred.

The Grignard reaction is conducted in an inert atmosphere, preferably in the presence of an inert solvent with a boiling point in the range $100°–120°$ C e.g. toluene or dioxan, toluene being the preferred solvent. The reaction may be carried out in the absence of a solvent but the yields are generally lower unless an excess of the Grignard reagent is used.

A method for preparing compounds of formula I in which X is $CO_2R^3$ comprises treating a compound of formula III with carbon dioxide to produce a compound of formula I wherein X is $CO_2M$ where M is as defined in connection with formula III and then with an alcohol $R^3OH$ wherein $R^3$ is lower alkyl group in the presence of an acid catalyst, e.g. dry HCl gas or conc. sulphuric acid. Compounds of formula I wherein X is $CO_2H$ may be obtained by treatment of a compound of formula (III) with acid e.g. hydrobromic or hydrochloric acid.

The esterification of a compound of formula I in which X is $CO_2H$ may be carried out using a hydroxyl compound $R^3OH$, wherein $R^3$ is lower alkyl according to standard procedures, e.g. in the presence of an acid catalyst e.g. some concentrated sulphuric acid or after saturation with hydrogen chloride gas or a Lewis acid e.g. boron trifluoride if desired with heat or treatment of the silver salt, (X is COOAg) with an iodide $R^3$ I wherein $R^3$ is lower alkyl.

When $R^6O$ and $R^5$ are not on the same carbon atom as X the yield of ester may be improved by treating a compound of formula I wherein X is hydrogen with a metal alkyl $MR^7$ followed by $CO_2$ then a further quantity of the metal alkyl after the $CO_2$ treatment, followed by a further amount of $CO_2$. It is believed that the further quantity of metal alkyl and $CO_2$ gives the bis acid metal salt of formula (IV)

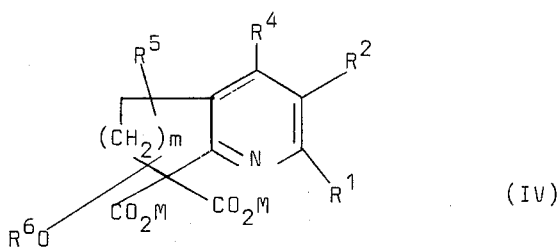

wherein $R^1$, $R^2$, $R^4$, $R^5$, $R^6$ and m are as defined in connection with formula I and M is sodium, potassium or lithium, and this salt spontaneously decarboxylates during the esterification.

A further method for preparing esters of formula I wherein X is $CO_2R^3$ comprises treating a compound of formula I as defined above wherein X is a hydrogen atom with a metal alkyl $MR^7$ and then treating the product with a haloformate of formula $HalCOOR^3$ wherein Hal is a halogen atom e.g. chlorine or bromine and $R^3$ is alkyl. When $R^6O$ and $R^5$ are not on the same carbon as X the product is usually a mixture of the desired compound of formula I wherein X is $CO_2R^3$ wherein $R^3$ is lower alkyl and the corresponding bis-ester of formula (V)

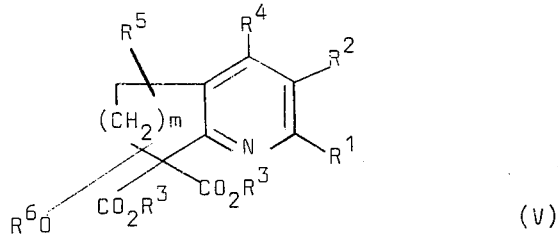

wherein $R^3$ is lower alkyl and $R^1$, $R^2$, $R^4$, $R^5$, $R^6$ and m are as defined in connection with formula I. These bis esters are useful for preparing the corresponding compounds of formula I wherein X is $CO_2H$. This mixture of mono and bis-esters may be converted directly to the corresponding compound of formula I where X is $CO_2H$, by saponification with an alkaline earth metal hydroxide to give a mixture of the metal salt of the mono acid of formula I wherein X is $CO_2H$ and the metal salt of the diacid of formula (VI) wherein $R^3$ is H. Treatment of this mixture with a mineral acid e.g. hydrochloric acid gives the desired acid of formula I wherein X is $CO_2H$ since the diacid spontaneously decarboxylates to form the mono acid.

The product of the haloformate reaction may be treated with a further quantity of the metal alkyl followed by a further quantity of the haloformate thereby producing more of the bis ester (V).

A further method for preparing compounds of formula I in which X is $CO_2H$ and $R^6O$ and $R^5$ are not on the same carbon atom as X comprises decarboxylation of a compound of formula (V). The decarboxylation may be carried out by heating the dicarboxylic acid of formula V wherein $R^3$ is hydrogen. Usually the dicarboxylic acid is prepared in situ by hydrolysis of the corresponding di-ester, wherein $R^3$ is lower alkyl. The hydrolysis and decarboxylation may be carried out by heating with a dilute mineral acid e.g. HCl or sulphuric acid or the diester may be saponified with alkali e.g. sodium or potassium hydroxide. The resulting salt is then acidified and decarboxylated by heating.

Compounds of formula I, in which X is $CONHR^3$ may be prepared by treatment of a corresponding compound of formula I wherein X is COCl or $CO_2R^3$ and $R^3$ is lower alkyl with ammonia to give a compound of formula I in which X is $CONH_2$, which may be subsequently alkylated to introduce the group $R^3$ when lower alkyl. Conveniently a compound of formula I wherein X is $CO_2R^3$ wherein $R^3$ is lower alkyl, especially methyl or ethyl, is treated with ammonia. Alternatively substituted amides of formula I wherein X is $CONHR^3$ wherein $R^3$ is lower alkyl may be prepared by treatment of the carboxylic ester of formula I wherein X is $CO_2R^3$ and $R^3$ is lower alkyl with an amine of formula $R^3NH_2$ wherein $R^3$ is lower alkyl. The substituted amides may also be prepared from the acid chloride of formula I wherein X is COCl by treatment with a primary amine $R^3NH_2$ wherein $R^3$ is lower alkyl.

Examples of primary amines which may be used in the above reactions are methylamine and n-butylamine.

The acid chlorides may be prepared by treatment of the corresponding acid formula I, wherein X is $CO_2H$ with thionyl chloride, phosphorus oxychloride or phosphorus pentachloride.

A further process for preparing compounds of formula I as defined above wherein X is $CONHR^3$ and $R^3$ is hydrogen or lower alkyl, comprises treating an ester compound of formula I, wherein X is $CO_2R^3$ and $R^3$ is lower alkyl with an amide of formula $R^9CONHR^3$ or a salt thereof wherein $R^3$ is hydrogen or lower alkyl and $R^9$ is hydrogen or lower alkyl in the presence of an alkali-metal alkoxide or sodamide.

Preferably a molar equivalent of alkali-metal alkoxide is used for each mole of ester of formula I. The alkali-metal alkoxide may be one derived from a lower alkanol having from 1 to 6 carbon atoms e.g. methanol or ethanol. The alkali-metal is preferably sodium.

The ester of formula I is preferably a lower alkyl ester.

The amide $R^9CONHR^3$ is preferably one in which $R^9$ is hydrogen or methyl. $R^3$ is also preferably hydrogen or methyl. Thus preferred amides are formamide, N-methylformamide, acetamide and N-methylacetamide. Salts, especially alkali-metal salts of these amides may be used as starting materials.

The reaction may be carried out by heating the reactants together.

The amides of formula I, wherein X is $CONH_2$ may also be prepared by partial hydrolysis of the corresponding nitriles of formula I, wherein X is CN. This hydrolysis may be accomplished in conventional manner e.g. by concentrated (e.g. 96%) sulphuric acid.

Thioamides of formula I wherein X is $CSNHR^3$ wherein $R^3$ is hydrogen or lower alkyl may be prepared by treatment of the corresponding compounds in which X is $CONHR^3$ with $P_2S_5$ e.g. by refluxing in pyridine. As mentioned below when the starting material is one in which X is $CONH_2$ decomposition to the nitrile may occur. This decomposition can be avoided by conducting the $P_2S_5$ reaction in the presence of $H_2S$. Alternatively the thioamides may be prepared by treatment of a nitrile of formula I, wherein X is CN with $H_2S$ to give the unsubstituted thioamide wherein X is $CSNH_2$. Substituted thioamides may be obtained by conducting this reaction in the presence of a primary amine $R^3NH_2$ wherein $R^3$ is lower alkyl. The $H_2S$ reaction can be carried out in a suitable solvent in the presence of a catalyst such as a tertiary amine e.g. a trialkylamine such as tri-ethylamine, or di-isopropylamine in ethanol.

The nitriles of formula I wherein X is CN, may be prepared by dehydration of the corresponding amides of formula I wherein X is $CONH_2$. Such dehydration can be carried out with $P_2O_5$ as the dehydrating agent. Other dehydrating agents are phosphorus pentachloride or thionyl chloride. Dehydration of an amide to a nitrile may be effected by heating the amide in hexamethyl-phosphorictriamide as solvent. When using this solvent a compound of formula I in which X is $CONMe_2$ may be formed as a significant by-product. The nitriles may also be formed when the amide is treated with $P_2S_5$. It is believed that the thioamide is first formed and decomposes to the nitrile. The nitrile can either be separated, e.g. by chromatography or the mixture treated with $H_2S$ for conversion of the nitrile to the corresponding thioamide.

A further method for preparing the thioamide of formula I, wherein X is $CSNH_2$ comprises reacting a nitrile of formula I wherein X is CN with a thioamide of formula $R^{10}CSNH_2$ where $R^{10}$ is an alkyl group, e.g. a lower-alkyl group of 1–6 carbon atoms, preferably a methyl group in a suitable solvent such as dimethyl formamide saturated with hydrogen chloride.

A further process for preparing compounds of formula I wherein X is $CSNHR^3$ and $R^3$ is lower alkyl comprises reacting a compound of formula III with a compound of formula $R^3NCS$ wherein $R^3$ is lower alkyl and then treating the product with hydrogen ions.

Preferably a starting material of formula III wherein M is lithium or MgHal is used. Conveniently the product after reaction with $R^3NCS$ is treated with acid e.g. an aqueous mineral acid such as a hydrohalic acid preferably hydrochloric acid. A preferred compound $R^3NCS$ is methyl isothiocyanate.

Substituted thioamides of formula I wherein X is $CSNHR^3$ and $R^3$ is lower alkyl may be prepared by treatment of a thioamide of formula I, wherein x is $CSNH_2$ with an amine of formula $R^3NH_2$ wherein $R^3$ is lower alkyl in the presence of $H_2S$.

Compounds of formula I wherein $R^6$ is hydrogen may be prepared by mild aminolysis e.g. with alcoholic ammonia or a lower alkylamine e.g. methylamine, of corresponding esters of formula I where $R^6$ is lower alkanoyl. Of course if X in the starting compound is $CO_2R^3$ where $R^3$ is lower alkyl then this ester group may be aminolysed to the primary or secondary amide.

Compounds of formula I wherein $R^6$ is lower alkyl may also be prepared by alkylation of the corresponding hydroxy compounds where $R^6$ is hydrogen e.g. by preparation of an alkali metal derivative such as the sodio derivative and treatment of this with a lower alkyl iodide or bromide. This procedure will usually alkylate a free $CONH_2$ or $CSNH_2$ group if present. If the free $CONH_2$ or $CSNH_2$ group is required then a compound where X is CN and $R^6$ is hydrogen can be alkylated and then the product treated either with $H_2S$ to give the thioamide where X is $CSNH_2$ or with Conc. sulphuric acid to partially hydrolyse the nitrile to the amide where X is $CONH_2$.

When X and $R^6O$ are on the same carbon atom then some of the interconversions of X groups discussed above may be prevented by steric hinderance. Thus conversion of the group X is $CO_2R^3$ where $R^3$ is lower alkyl to the corresponding amide may not be possible where the carbon atom carrying X also carries the group $R^6O$. However the desired compound can be made by an alternative route as will be discussed below. Also conversion of the amide (X is $CONHR^3$) to the corresponding thioamide (X is $CSNHR^3$) using $P_2S_5$ may be prevented when X carries $R^6O$ but the desired compound can be made by an alternative route as will also be discussed below.

Compounds of formula I wherein X is $CSNHR^3$ and $R^3$ is lower alkyl and $R^6O$ is present on the same carbon atom as X, $R^6$ being lower alkyl may be prepared by the following scheme

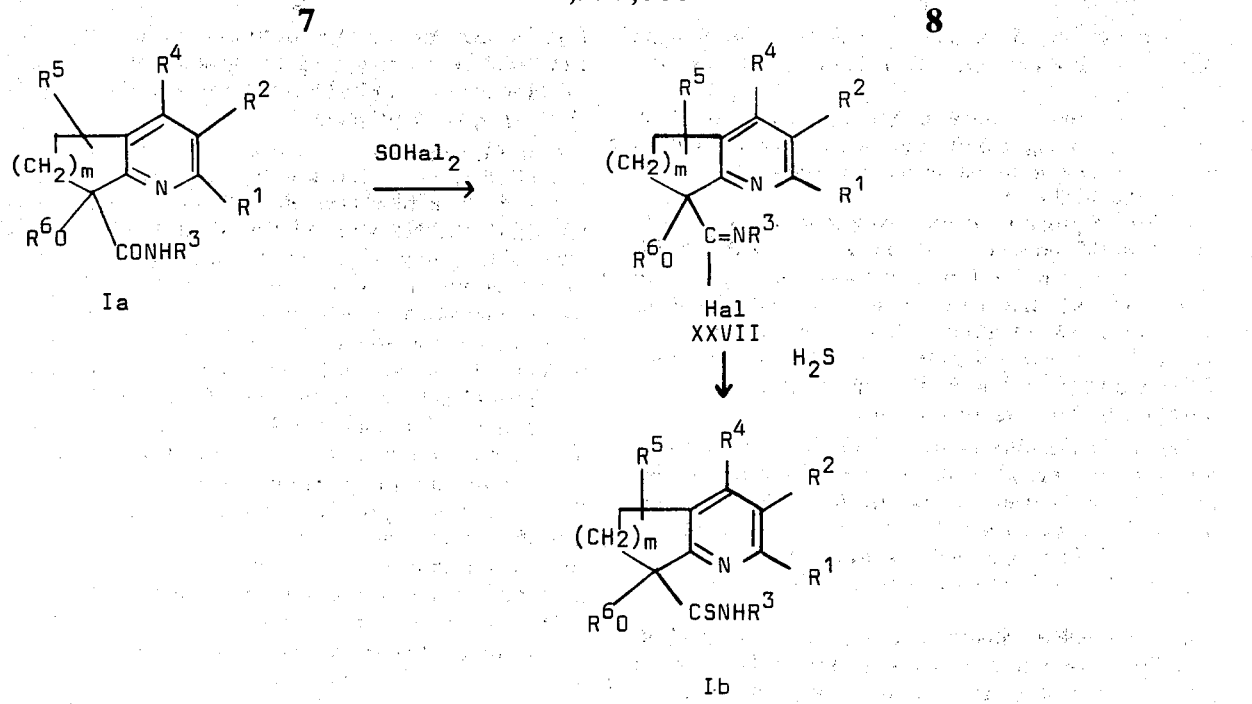

In this scheme the amide Ib wherein $R^1$, $R^2$, $R^4$, $R^5$ and $m$ are as defined in connection with formula I and $R^3$ and $R^6$ are lower alkyl is treated with a compound of formula $SOHal_2$ where Hal denotes chlorine or bromine (i.e. thionyl chloride or thionyl bromide) to give the corresponding imidoylhalide XXVII which is treated with $H_2S$ to give the thioamide IB.

The starting materials of formula I wherein X is hydrogen are either known compounds or may be prepared by processes for preparing analogous compounds.

One method for preparing starting materials of formula I wherein X is hydrogen and $R^6$ is lower alkyl or lower alkanoyl comprises alkylating or acylating corresponding hydroxy compound of formula (VI)

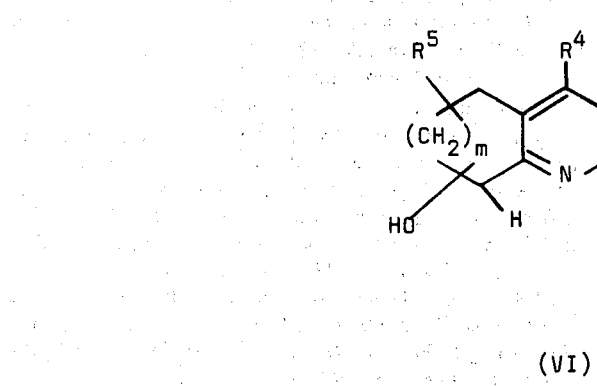

(VI)

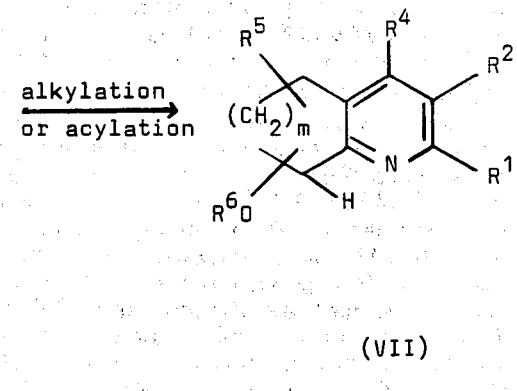

(VII)

to introduce the group $R^6$. The starting hydroxy compounds (VI) are either known compounds or may be prepared by methods known for analogous compounds. One method comprises reacting a cycloalkane dione (VIII) wherein $m$ is 1, 2, or 3

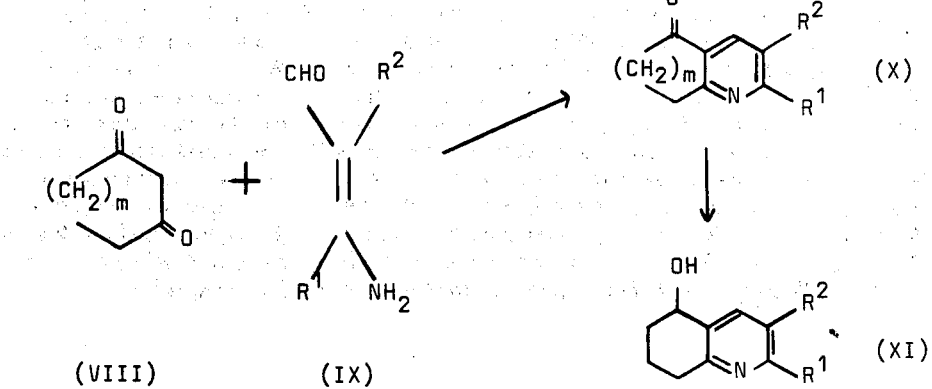

with an aldehyde of formula (IX) to give an oxo compound of formula (X) which is reduced e.g. with sodium borohydride to give the hydroxy compound (XI) which may then be alkylated. The cycloalkane dione (VIII) may be substituted by an $R^5$ group to give an appropriately substituted starting material of formula I wherein X is hydrogen.

A method for preparing 6-alkoxy 5,6,7,8-tetrahydroquinoline starting compounds of formula I, wherein X is hydrogen comprises condensing a compound of formula XII with a compound of formula XIII 7, 8-tetrahydroquinoline starting materials comprises reacting a compound of formula (XV)

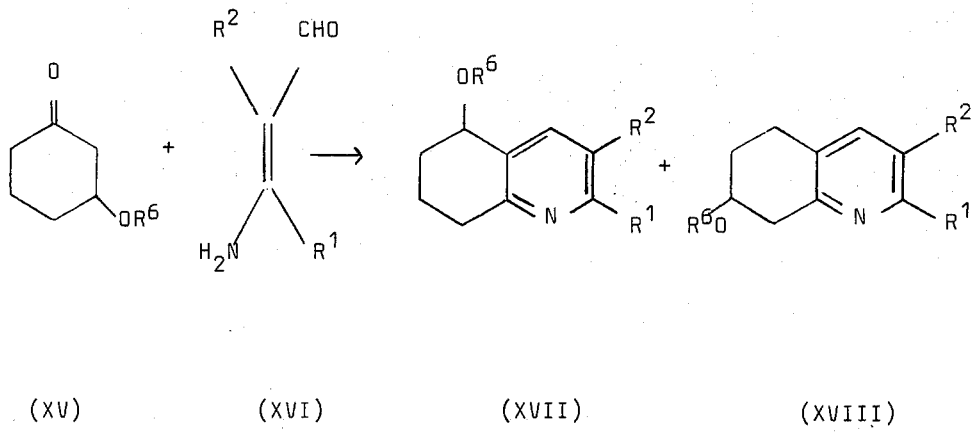

(XV)　　(XVI)　　(XVII)　　(XVIII)

with a compound of formula (XVI) to give a mixture of the 5-alkoxy 5,6,7,8-tetrahydroquinoline of formula (XVII) and the 7-alkoxy, 5,6,7,8-tetrahydroquinoline of formula (XVIII). This mixture is then separated e.g. by chromatography. In the above scheme $R^1$, $R^2$ and $R^6$ are as defined in connection with formula I. 8-Alkoxy 5,6,7,8-tetrahydroquinolines may be prepared by oxidising the corresponding 5,6,7,8-tetrahydroquinoline (XIX) to the N-oxide (XX) which is then rearranged to the 8-acyloxy compound (XXI) by treatment with an

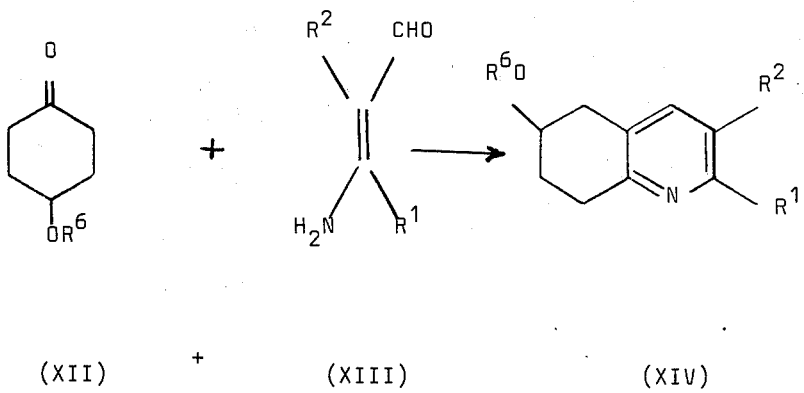

(XII)　+　(XIII)　　(XIV)

In the above scheme $R^1$, $R^2$ and $R^6$ are as defined in connection with formula I.

A further method for preparing 5 and 7-alkoxy 5, 6, 7, 8-tetrahydroquinoline starting materials comprises acid anhydride. The 8-acyloxy compound is then hydrolysed to the 8-hydroxy compound XXII and alkylated to give the 8-alkoxy compound (XXIII)

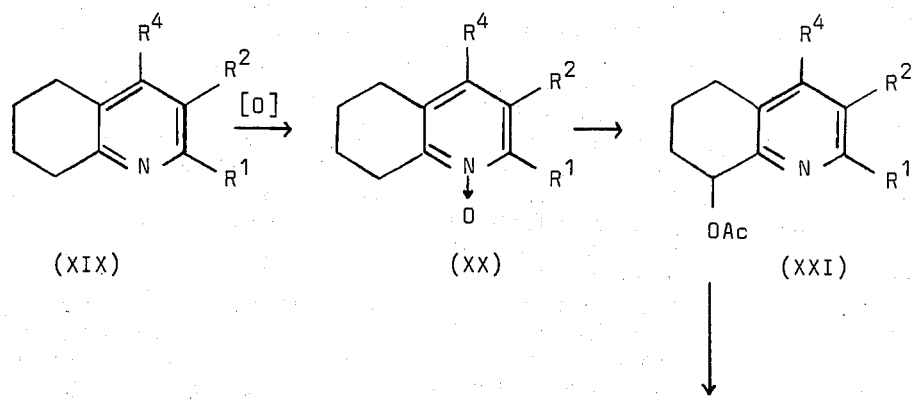

(XIX)　　(XX)　　(XXI)

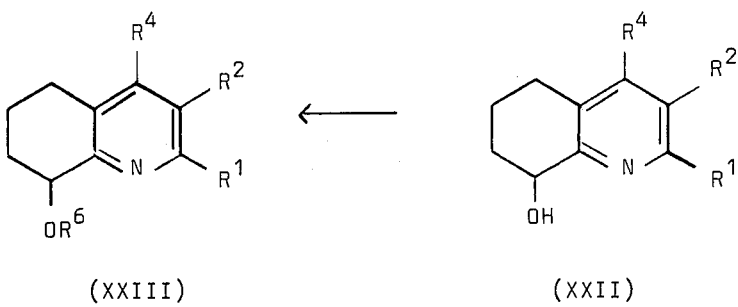

An analogous route may also be used to prepare compounds of formula I wherein X is present on the same carbon atom as $R^6O$. This scheme is shown below to obtain another compound of formula I. Thus a nitrile where X is CN may be treated with $H_2S$ to give the corresponding thioamide. In this way a thioamide of

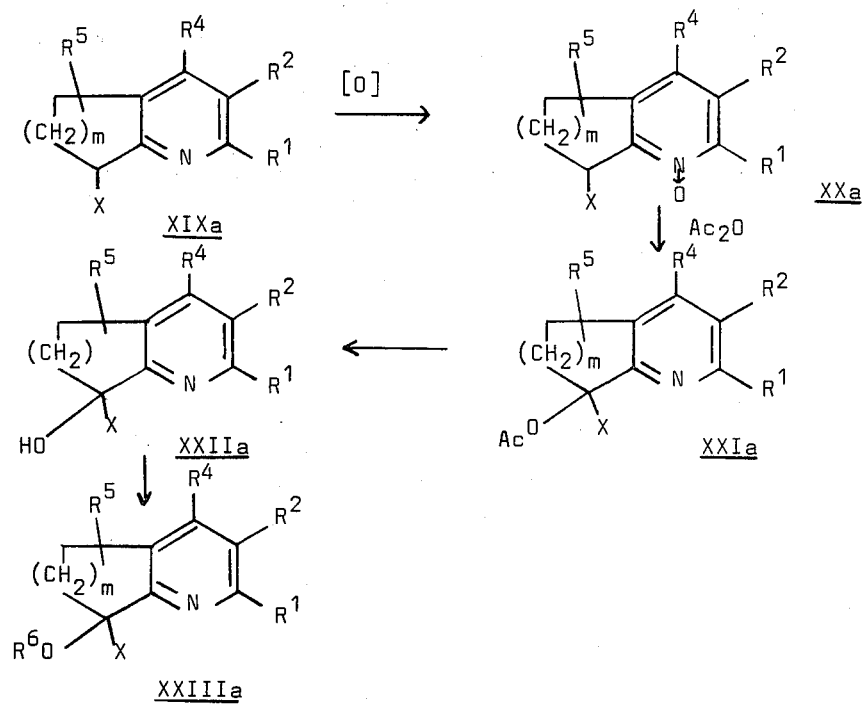

The compound of formula XIXa wherein $R^1$, $R^2$, $R^4$ and m are as defined in connection with formula I and X is CN, $CONHR^3$ or $CO_2R^3$ and $R^3$ is as defined in connection with formula I is oxidised with hydrogen peroxide or a per acid such as m-chloroperbenzoic acid to give the N-oxide XXa which is rearranged by treatment with a lower alkanoic acid anhydride e.g. acetic anhydride to give the lower alkanoic ester XXa which is subjected to mild hydrolysis or aminolysis e.g. with alcoholic ammonia or a lower alkyl-amine e.g. methylamine to give the hydroxy compound XXIIa which is then alkylated e.g. by formation of an alkali metal derivative which is then treated with a lower alkyl iodide or bromide to give the alkoxy compound XXIIIa where $R^6$ is lower alkyl. The group x is in compound XXIa, XXIIa or XXIIIa may be converted to another group X formula XXIa where X is $CSNH_2$ may be prepared and converted to the corresponding thioamide of formula XXIIa and then to a thioamide of formula XXIIIa. The alkylation step will usually result in alklation of an amide to give an amide of formula XXIIIa where X is $CONHR^3$ and $R^3$ is lower alkyl. The primary thioamide of formula XXIIIa where X is $CSNH_2$ may be prepared by making a compound of formula XXIIIa where X is CN and treating this with $H_2S$. Similarly the primary amide of formula XXIIa where X is $CONH_2$ may be prepared by preparation of the nitrile of formula XXIIIa where X is CN and treating this with conc. $H_2SO_4$ to achieve partial hydrolysis to the amide.

A further method for preparing 7-alkoxy 5,6,7,8-tetrahydroquinolines comprises reacting an alkoxy cyclohexane dione (XXIIa)

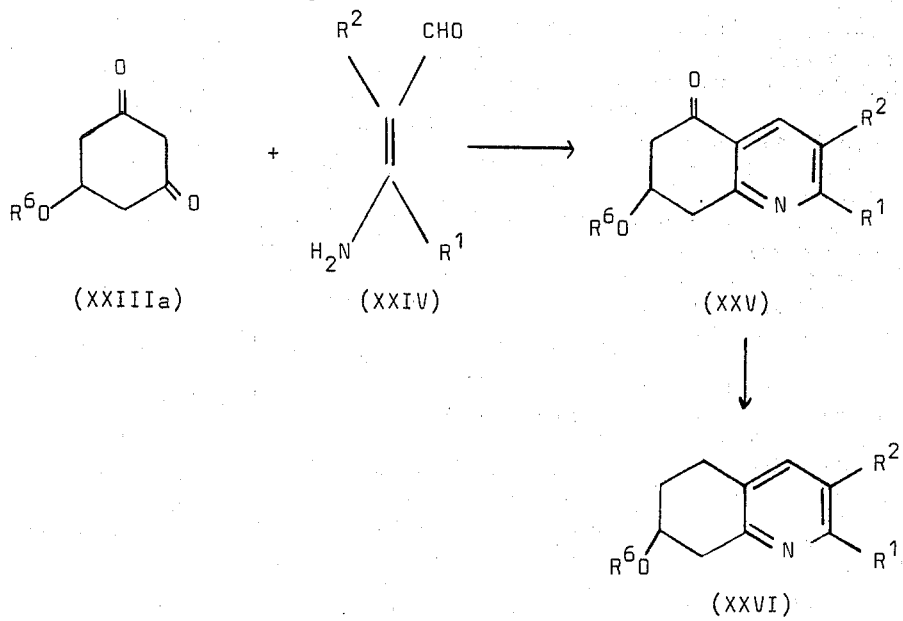

with an amino aldehyde (XXIV) to give a 5-oxo compound (XXV) which is then reduced to the 7-alkoxy compound (XXVI), wherein $R^1$, $R^2$ and $R^6$ are as defined in connection with formula I.

The invention also includes pharmaceutical compositions comprising a compound of formula I wherein X is $CSNHR^3$ or cyano and a pharmaceutical carrier.

For the pharmaceutical carrier any suitable carrier known in the art can be used to prepare the pharmaceutical compositions. In such a composition, the carrier may be a solid, liquid or mixture of a solid and a liquid.

Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating mateial as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in a suitable organic solvent, for instance aqueous propylene glycol containing from 10 to 75% of the glycol by weight is generally suitable.

In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be packaged composition, the package containing specific quantites of compositions, for example packeted powders or vials or ampoules. The unit dosage form can be a capsule, cachet or table itself, or it can be the appropriate number of any of these in packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The anti-ulcer compositions of the invention will be adminstered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

The following Examples illustrate the invention.

EXAMPLE I

8-Carboxamido-3-methyl-5,6,7,8-tetrahydroquinoline-1-oxide i. 3-Methyl-5,6,7,8-tetrahydroquinoline-8-carboxamide (29 g) was dissolved in acetic acid and the mixture was treated with hydrogen peroxide (100 vol, 32 ml) and heated with stirring at 80° for 3 hours. A further portion of hydrogen peroxide (15 ml) was added and the heating was continued for 15 hours at 80° C. The reaction mixture was evaporated in vacuo and the residue diluted with water and re-evaporated. The residue was dissolved in chloroform and extracted with sodium carbonate solution and water. The aqueous extract was ajusted to pH 7 with acetic acid and continuously extracted with chloroform for 18 hours. The chloroform solution was dried (MgSO₄) and evaporated to give a solid (19 g) which was recrystallised from benzene to give the title compound (m.p. 208°). Found: C, 64.4; H, 6.9; N, 13.6. $C_{11}H_{14}N_2O_2$ requires: C, 64.1; H, 6.8; N, 13.6%.

ii. A stirred solution of 3-methyl-5,6,7,8-tetrahydroquinoline-8-carboxamide (19 g) in methylene chloride (100 ml) was treated dropwise with a solution of m-chloroperbenzoic acid (17.25 g) in methylene chloride (150 ml) and the mixture was stirred overnight at ambient temperature. The methylene chloride solution was extracted with sodium carbonate and brine and the aqueous extracts were acidified with conc. HCl and filtered.

The filtrate was adjusted to pH 9 with sodium carbonate solution and to pH 7 with acetic acid and then continously extracted with chloroform for 24 hours. The chloroform solution was dried ($MgSO_4$) and evaporated to give a residue (12.5 g) which was recrystallised from benzene to give the title compound (8g).

EXAMPLE 2

8-Acetoxy-3-methyl-5,6,7,8-tetrahydroquinoline-8-carboxamide

8-Carboxamido-3-methyl-5,6,7,8-tetrahydroquinoline-1-oxide (2.6g) was added portion wise to acetic anhydride (13 ml) at 90° C. The reaction mixture was heated at 120° C for 30 min. during which time the solid dissolved and the product precipitated. The reaction mixture was cooled to 0° C and the solid (2 g) was removed by filtration and washed with dry ether. Recrystallisation from methanol gave the title compound as pale yellow needles (m.p. 205°). Found: C, 62.7; H, 6.6; N, 11.2 $C_{13}H_{16}N_2O_3$ requires: C, 62.9; H, 6.5; N, 11.3%.

EXAMPLE 3

8-Hydroxy-3-methyl-5,6,7,8-tetrahydroquinoline-8-carboxamide

8-Acetoxy-3-methyl-5,6,7,8-tetrahydroquinoline-8-carboxamide (0.8 g) was added to a solution of ammonia in methanol (150 ml) at 0° C and the resulting suspension was stirred at ambient temperature for 18 hours in a sealed flask during which time the solid dissolved. The solution was evaporated to dryness in vacuo and the resulting oily solid was dissolved in 2N HCl and the solution was washed with ethyl acetate. The aqueous solution was adjusted to pH 9 with sodium carbonate and extracted with ethyl acetate and chloroform. The organic solutions were dried ($MgSO_4$) and evaporated to give a solid (0.46 g) which was recrystallised from ethyl acetate to give the title compound as the hemi-hydrate (m.p. 118° C). Found: C, 61.7; H, 7.0; N, 13.0 $C_{11}H_{14}N_2O_2$. ½$H_2O$ requires: C, 61.5; H, 7.0; N, 13.0%.

EXAMPLE 4

8-Methoxy-3-methyl-5,6,7,8-tetrahydroquinoline-8-(N-methyl) carboxamide

To a suspension of 8-hydroxy-3-methyl-5,6,7,8-tetrahydroquinoline-8-carboxamide (1.3 g) in dimethoxyethane (10 ml) was added sodium hydride (60% dispersion in oil, 0.25 g) and the mixture was stirred for ½ hour at room temperature and 45 mins. at 45° C. The reaction mixture was cooled to 0° C and treated dropwise with a solution of methyl iodide (1 g) in dimethoxy-ethane (1.5 ml) and allowed to stand at room temperature for 1 hour. It was then diluted with water and extracted with chloroform. The chloroform solution was dried ($MgSO_4$) and evaporated under reduced pressure to give an oil which was dissolved in ether and converted into the hydrochloride by addition of ethereal solution of HCl. The resulting solid was recrystallised from isopropyl alcohol/di-isopropyl ether to give the title compound, hydrochloride, 1.1/4 hydrate (m.p. 124° C). Found: C, 53.4; H, 7.4; N, 9.8. $C_{13}H_{18}N_2O_2$.HCl.1.1/4$H_2O$ requires: C, 53.3; H, 7.3; N, 9.6%.

EXAMPLE 5

8-Methoxy-3-methyl-5,6,7,8-tetrahydroquinoline-8-(N-methyl)-thiocarboxamide

Thionyl chloride (0.9 ml) was added dropwise to a solution of 8-methoxy-3-methyl-5,6,7,8-tetrahydroquinoline-8-(N-methyl) carboxamide (1.6 g) in pyridine (10 ml) at 0° C to form 8-methoxy-3-methyl-5,6,7,8-tetrahydroquinoline-8-(N-methyl)-imidoyl-chloride. After 4 hours the reaction mixture was treated with $H_2S$ gas for 5 min. and the mixture was allowed to stand at room temperature for 3 days. The solvent was evaporated under reduced pressure and the residue was dissolved in water. The resulting solution was basified with sodium carbonate and extracted with chloroform. The chloroform solution was dried ($MgSO_4$) and evaporated under reduced pressure and the resulting oil was chromatographed on silica with ethyl acetate as eluent to give a solid which was recrystallised from hexane to give the title compound (0.1 g, m.p. 104° C). Found: c, 62.1; H, 7.4; N, 11.0. $C_{13}H_{18}N_2SO$ requires C, 62.4; H, 7.2; N, 11.2%.

EXAMPLE 6

8-Cyano-3-methyl-5,6,7,8-tetrahydroquinoline-1-oxide

Using the procedure of Example 1 part ii, 8-cyano-3-methyl-5,6,7,8-tetrahydroquinoline was converted into the title compound (m.p. 136° C ex benzene/light petroleum b.p. 40°/60°). Found: C, 70.4; H, 6.7; N, 15.1 $C_{11}H_{12}N_2O$ requires: C, 70.2; H, 6.4; N, 14.9%.

EXAMPLE 7

8-Acetoxy-8-cyano-3-methyl-5,6,7,8-tetrahydroquinoline

Using the procedure of Example 2, 8-cyano-3-methyl-5,6,7,8-tetrahydroquinoline-1-oxide was converted into the title compound and isolated as the hydrochloride, quarter hydrate (m.p. 84° C). Found: C, 57.9; H, 6.2; N, 10.4. $C_{13}H_{14}N_2O_2$.HCl.1/4$H_2O$ requires: C, 57.6; H, 5.8; N, 10.3%.

EXAMPLE 8

8-Acetoxy-3-methyl-5,6,7,8-tetrahdyroquinoline-8-thiocarboxamide

A solution of 8-acetoxy-8-cyano-3-methyl-5,6,7,8-tetrahydroquinoline (2g) in pyridine (20 ml) and triethylamine (6 ml) was saturated with $H_2S$ gas and allowed to stand at room temperature for 2 days. The solvent was removed by evaporation, benzene (20 ml) was added and the mixture was re-evaporated. Benzene (20 ml) was added and the solution was filtered and the filtrate was extracted with 2N HCl. The acid solution was washed with benzene, basified with sodium carbonate and extracted with benzene. The benzene solution was dried ($MgSO_4$) and evaporated under reduced pressure. The residue was extracted with di-isopropyl ether and the extract was allowed to evaporate slowly depositing a sticky solid which was triturated with isopropyl alcohol to give the title compound, quarter hydrate. (m.p. 116°–8° C). Found: C, 58.15; H, 6.2; N, 10.4%. $C_{13}H_{16}N_2O_2S$ requires: C, 58.1; H, 6.2; N, 10.4%.

EXAMPLE 9

8-Hydroxy-3-methyl-5,6,7,8-tetrahydroquinoline-8-thiocarboxamide

Using the procedure of Example 3, 8-acetoxy-3-methyl-5,6,7,8-tetrahydroquinoline-8-thiocarboxamide is converted into the title compound.

EXAMPLE 10

Methyl-3-methyl-5,6,7,8-tetrahydroquinoline-8-carboxylate-N-oxide

Methyl-3-methyl-5,6,7,8-tetrahydroquinoline-8-carboxylate (58 g) was dissolved in acetic acid (180 ml.) and the mixture treated with 100 vol. hydrogen peroxide (65 ml). The mixture was heated with stirring at 80° for 3 hours. A further portion of 100 vol. hydrogen peroxide (30 ml) was added and the mixture heated at 80° for 15 hours. A further portion of 100 vol. $H_2O_2$ (15 ml) is added and the mixture heated at 80° for 6 hours and then evaporated to dryness. The residue was treated with water and evaporated to dryness. The residue was dissolved in chloroform, washed with sodium carbonate solution, water, then brine, dried and evaporated to give the title compound (53 g).

EXAMPLE 11

8-Acetoxy-methyl-3-methyl-5,6,7,8-tetrahydroquinoline-8-carboxylate

The N-oxide of Example 10 (53 g.) was dissolved in acetic anhydride (130 ml) and added dropwise to boiling acetic anhydride (130 ml). The mixture was heated at reflux for 30 minutes, cooled and evaporated to dryness. The residue was dissolved in water, basified with $Na_2CO_3$ and extracted with chloroform. The combined extracts were dried and evaporated to give an oil which was distilled at 0.05 mm Hg to give the title compound bp 170° C/0.05 mm

EXAMPLE 12

5-Methoxy-3-methyl-5,6,7,8-tetrahydroquinoline-8-thiocarboxamide

A solution of 5-methoxy-3-methyl-5,6,7,8-tetrahydroquinoline (3.5 g., 0.02 mol) in dry benzene (10 ml) is cooled to −20° C and treated dropwise with a 10% (w/v) solution of n-butyl lithium in hexane (14 ml., 0.022 mol) under nitrogen. After 10 min. at −20° C a slow stream of dry $CO_2$ gas is bubbled into the reaction mixture until it becomes colourless. The reaction mixture is then diluted with water, filtered and the aqueous phase extracted with ether (3 times). The aqueous phase is evaporated to dryness and the residual solid treated with a solution of methanol previously saturated with dry HCl gas and allowed to stand at room temperature for 12 hours. The volatiles are removed in vacuo. The residual oil is redissolved in water, extracted with ether (3times) and the ether extracts discarded. The aqueous solution is adjusted to pH 9 with sodium carbonate and extracted with ether (4 times). The combined ether extracts are dried and the solvent removed in vacuo to give methyl 5-methoxy-3-methyl-5,6,7,8-tetrahydroquinoline 8-carboxylate. The carboxylate (1 mol) is heated with formamide (2 mols) and sodium methoxide (1 mol) at 120° C for 1 hour while bubbling nitrogen through the mixture to blow off the methyl formate produced in the reaction.

The cooled reaction mixture is diluted with 2N HCl to give an acidic solution which is extracted with ethylacetate and the extracts discarded. The aqueous solution is adjusted to pH 9 with solid sodium carbonate, saturated with sodium chloride and extracted with chloroform. The extracts are dried and evaporated to give 5-methoxy-5,6,7,8-tetrahydroquinoline-8-carboxamide which is dissolved in dry pyridine saturated with $H_2S$ gas and treated with a molar equivalent amount of $P_2S_5$ and heated under reflux for 45 minutes; whilst maintaining a slow stream of $H_2S$ gas. The reaction mixture is evaporated to dryness in vacuo, cooled to 0° C, made alkaline with 10% sodium hydroxide and the solution extracted with chloroform (3 times). The extracts are washed with brine, dried and evaporated in vacuo to give the title compound.

I claim:

1. A compound of the formula

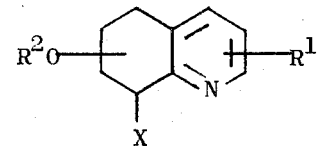

and the non-toxic acid addition salts thereof wherein $R^1$ is hydrogen or alkyl of from 1 to 6 carbon atoms, $R^2$ is hydrogen, alkyl of from 1 to 6 carbon atoms or carboxylic acyl of from 1 to 6 carbon atoms, X is CN, $CONHR^3$, $CSNHR^3$, or $CO_2R^3$ wherein $R^3$ is hydrogen or alkyl of from 1 to 6 carbon atoms, or an alkali metal salt of a compound in which X is COOH.

2. A compound as claimed in claim 1 wherein X is $CSNH_2$ or $CSNHCH_3$

3. A compound as claimed in claim 1, which is 5-methoxy-3-methyl-5,6,7,8-tetrahydroquinoline-8-thiocarboxamide.

4. A compound as claimed in claim 1, which is 8-acetoxy-3-methyl-5,6,7,8-tetrahydroquinoline-8-carboxamide.

5. A compound as claimed in claim 1, which is 8-hydroxy-3-methyl-5,6,7,8-tetrahydroquinoline-8-carboxamide.

6. A compound as claimed in claim 1, which is 8-methoxy-3-methyl-5,6,7,8-tetrahydroquinoline-8-(N-methyl)carboxamide or a pharmaceutically acceptable acid addition salt thereof.

7. A compound as claimed in claim 1, which is 8-methoxy-3-methyl-5,6,7,8-tetrahydroquinoline-8-(N-methyl)thiocarboxamide.

8. A compound as claimed in claim 1, which is 8-acetoxy-8-cyano-3-methyl-5,6,7,8-tetrahydroquinoline or a pharmaceutically acceptable acid addition salt thereof.

9. A compound as claimed in claim 1 which is 8-acetoxy-3-methyl-5,6,7,8-tetrahydroquinoline-8-thiocarboxamide.

* * * * *